(12) United States Patent
Chernov et al.

(10) Patent No.: US 9,456,870 B2
(45) Date of Patent: Oct. 4, 2016

(54) OPTICAL ENERGY-BASED METHODS AND APPARATUS FOR TISSUE SEALING

(75) Inventors: Boris Chernov, Saint-Petesburg (RU); Nataliya Chernova, legal representative, Saint-Petersburg (RU); Igoris Misuchenko, Saint-Petersburg (RU); Georgy Martsinovskiy, Saint-Petersburg (RU); Mikhail Verbitsky, Stoughton, MA (US)

(73) Assignee: Covidien LP, Mansfield, MA (US)

( * ) Notice: Subject to any disclaimer, the term of this patent is extended or adjusted under 35 U.S.C. 154(b) by 200 days.

(21) Appl. No.: 13/108,152

(22) Filed: May 16, 2011

(65) Prior Publication Data
US 2012/0296323 A1   Nov. 22, 2012

(51) Int. Cl.
*A61B 18/20* (2006.01)
*A61B 17/29* (2006.01)
(Continued)

(52) U.S. Cl.
CPC ............... *A61B 18/20* (2013.01); *A61B 17/29* (2013.01); *A61B 17/295* (2013.01); *A61B 2018/0063* (2013.01); *A61B 2018/00702* (2013.01); *A61B 2018/00791* (2013.01); *A61B 2018/00875* (2013.01); *A61B 2018/2065* (2013.01); *A61B 2018/2266* (2013.01); *A61B 2018/2272* (2013.01); *A61B 2018/2294* (2013.01)

(58) Field of Classification Search
CPC ................... A61B 2018/0063; A61B 17/295; A61B 18/20; A61B 17/29; A61B 2018/00702; A61B 2018/00791; A61B 2018/00875; A61B 2018/2065; A61B 2018/2266; A61B 2018/2272; A61B 2018/2294

USPC .......................... 606/7–8, 14–16; 607/88–94
See application file for complete search history.

(56) References Cited

U.S. PATENT DOCUMENTS

D249,549 S    9/1978  Pike
4,126,136 A   11/1978 Auth
(Continued)

FOREIGN PATENT DOCUMENTS

CN    201299462    9/2009
DE    2415263      10/1975
(Continued)

OTHER PUBLICATIONS

U.S. Appl. No. 08/926,869, filed Sep. 10, 1997, James G. Chandler.
(Continued)

*Primary Examiner* — Gary Jackson
*Assistant Examiner* — Scott T Luan

(57) ABSTRACT

Optical energy-based methods and apparatus for sealing vascular tissue involves deforming vascular tissue to bring different layers of the vascular tissue into contact each other and illuminating the vascular tissue with a light beam having at least one portion of its spectrum overlapping with the absorption spectrum of the vascular tissue. The apparatus may include two deforming members configured to deform the vascular tissue placed between the deforming members. The apparatus may also include an optical system that has a light source configured to generate light, a light distribution element configured to distribute the light across the vascular tissue, and a light guide configured to guide the light from the light source to the light distribution element. The apparatus may further include a cutting member configured to cut the vascular tissue and to illuminate the vascular tissue with light to seal at least one cut surface of the vascular tissue.

17 Claims, 6 Drawing Sheets

(51) Int. Cl.
    *A61B 17/295* (2006.01)
    *A61B 18/00* (2006.01)
    *A61B 18/22* (2006.01)

(56) References Cited

U.S. PATENT DOCUMENTS

| | | | |
|---|---|---|---|
| 4,266,547 A | 5/1981 | Komiya | |
| 4,273,127 A * | 6/1981 | Auth et al. | 606/3 |
| D263,020 S | 2/1982 | Rau, III | |
| 4,627,435 A * | 12/1986 | Hoskin | 606/28 |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 4,854,320 A | 8/1989 | Dew et al. | |
| 5,071,417 A | 12/1991 | Sinofsky | |
| 5,147,356 A | 9/1992 | Bhatta | |
| D343,453 S | 1/1994 | Noda | |
| D348,930 S | 7/1994 | Olson | |
| D349,341 S | 8/1994 | Lichtman et al. | |
| 5,334,191 A | 8/1994 | Poppas et al. | |
| 5,336,221 A * | 8/1994 | Anderson | 606/27 |
| 5,342,358 A | 8/1994 | Daikuzono | |
| D354,564 S | 1/1995 | Medema | |
| 5,409,481 A | 4/1995 | Poppas et al. | |
| D358,887 S | 5/1995 | Feinberg | |
| 5,470,331 A | 11/1995 | Daikuzono | |
| D384,413 S | 9/1997 | Zlock et al. | |
| 5,662,643 A | 9/1997 | Kung et al. | |
| 5,762,609 A | 6/1998 | Benaron et al. | |
| 5,769,791 A | 6/1998 | Benaron et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| 6,039,729 A * | 3/2000 | Durville et al. | 606/16 |
| D424,694 S | 5/2000 | Tetzlaff et al. | |
| D425,201 S | 5/2000 | Tetzlaff et al. | |
| 6,086,586 A | 7/2000 | Hooven | |
| H1904 H | 10/2000 | Yates et al. | |
| 6,221,069 B1 | 4/2001 | Daikuzono | |
| 6,248,117 B1 | 6/2001 | Blatter | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,569,173 B1 | 5/2003 | Blatter et al. | |
| 6,623,494 B1 | 9/2003 | Blatter | |
| 6,673,065 B1 * | 1/2004 | Veligdan | 606/16 |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| 6,974,452 B1 * | 12/2005 | Gille et al. | 606/37 |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,452,355 B2 | 11/2008 | Khomchenko | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 2004/0176752 A1 | 9/2004 | Alfano et al. | |
| 2005/0234437 A1 | 10/2005 | Baxter et al. | |
| 2005/0261568 A1 | 11/2005 | Hular et al. | |
| 2007/0179484 A1 | 8/2007 | Sade | |
| 2008/0077200 A1 * | 3/2008 | Bendett et al. | 607/89 |
| 2008/0221409 A1 | 9/2008 | Hoarau | |
| 2008/0319442 A1 * | 12/2008 | Unger et al. | 606/48 |
| 2009/0234347 A1 * | 9/2009 | Treat et al. | 606/30 |
| 2009/0287194 A1 | 11/2009 | Gertz et al. | |
| 2010/0049187 A1 | 2/2010 | Carlton et al. | |
| 2010/0160904 A1 | 6/2010 | McMillan | |
| 2010/0217258 A1 | 8/2010 | Floume et al. | |
| 2013/0253489 A1 | 9/2013 | Nau, Jr. et al. | |
| 2014/0121508 A1 | 5/2014 | Latimer et al. | |
| 2014/0288541 A1 | 9/2014 | Eshkol et al. | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 0480293 A1 | 4/1992 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |

(56) References Cited

FOREIGN PATENT DOCUMENTS

| | | |
|---|---|---|
| JP | 2004-517668 | 6/2004 |
| JP | 2004-528869 | 9/2004 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, fled Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.

(56) References Cited

OTHER PUBLICATIONS

Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l. Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.

(56) References Cited

OTHER PUBLICATIONS

Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
International Search Report PCT/US2012/038112, dated Jul. 16, 2012.
International Search Report PCT/US2012/038126, dated Jul. 16, 2012.
International Search Report PCT/US2012/038104, dated Jul. 10, 2012.

* cited by examiner

OPTICAL ENERGY-BASED METHODS AND APPARATUS FOR TISSUE SEALING

BACKGROUND

1. Technical Field

The present disclosure is directed to tissue sealing and, in particular, to systems and methods for tissue sealing employing optical energy.

2. Background of Related Art

Existing energy-based surgical systems and methods use electrical energy or ultrasound energy to heat tissue (see, e.g., U.S. Pat. Nos. 7,384,420 and 7,255,697, and U.S. Patent Application Publication Nos. 2008/0147106 and 2009/0036912). For example, electrosurgical systems include an electrosurgical generator for producing high frequency electrical energy (e.g., radio frequency (RF) or microwave (MW) energy) and an electrosurgical instrument for applying the electrical energy to tissue. A surgeon may use the electrosurgical instrument to cut, coagulate, desiccate, and seal tissue.

Existing energy-based surgical methods and systems, however, may have several disadvantages that limit their performance and effectiveness. First, they may limit the surgeon's ability to control and localize energy in tissue. As a result, the energy thermally damages tissue adjacent to the target tissue. Also, energy is lost because an excessive volume of tissue is heated (i.e., both the target tissue and the adjacent tissue are heated).

Second, existing energy-based devices require direct physical contact between the tissue and the electrodes, ultrasound transducers, or sound-conducting portions of the surgical instrument to transmit energy to the tissue. As a result, a significant amount of energy is lost to the environment and to that portion of the instrument in contact with the heated tissue, while only a small amount of energy is used to actually heat tissue. Also, tissue may attach to that portion of the energy-based instrument that is in contact with the tissue.

Third, existing energy-based instruments may obstruct the surgeon's view of the target tissue or the operating site. Fourth, existing energy-based instruments typically include a large generator and a significant amount of wiring.

Lastly, electromagnetic energy-based systems and methods (e.g., RF- and MW-energy-based systems and methods) may cause stray currents, flashovers (e.g., an electric arc between the instrument and the tissue), short circuits in the conducting environment, and/or electromagnetic interference with other tissues and devices.

There are a number of laser-based surgical instruments, such as laser scalpels, that use laser radiation to cut and coagulate tissue. One disadvantage of laser scalpels is that they cannot seal relatively large vessels because laser scalpels cannot bring together opposite walls of the vessels. For example, in the article, Rodney A. White, et al., "Large vessel sealing with the argon laser," Lasers in Surgery and Medicine 7, pages 229-235 (1987), the edges of damaged vessels are first approached to each other and then sealed by exposing them to laser radiation.

There are also devices that use light to perform tissue ablation procedures. For example, as described in U.S. Pat. No. 4,266,547, tissue is placed between transparent holders through which the light is introduced to the tissue. The absorption of light by the tissue causes heating, charring, and ablation of the tissue. In optical ablation, the tissue can be illuminated with propagating waves or evanescent waves resulting from total external reflection. See, e.g., Cox, et al., "New method for exposing mammalian cells to intense laser radiation using the evanescent fields created in optical waveguides," Med. Phys. 5:274-279 (1978).

There are also instruments for coagulating blood vessels through the skin without deforming or damaging the tissue. For example, U.S. Pat. No. 7,452,355 describes simultaneously using multiple wavelengths of light radiation so that the radiation of one of the wavelengths modifies the blood and creates in the blood centers of high absorption of the radiation of other wavelengths, which can penetrate deeper into the tissue and completely seal the vessel.

The optical methods and systems described above, however, may not provide high quality vascular tissue sealing, especially for relatively large vessels.

SUMMARY

The surgical systems and methods according to embodiments of the present disclosure provide efficient sealing of vascular tissue including large vessels and mitigate the disadvantages of existing methods and devices, which are based on RF current, ultrasound, or optical radiation.

In one aspect, the present disclosure features a method of sealing vascular tissue. The method includes deforming vascular tissue to cause different layers of the vascular tissue to contact each other and illuminating at least one portion of the vascular tissue with light having at least one portion of the light's spectrum overlapping with an absorption spectrum of the vascular tissue. The light may include at least a first light wave having a first wavelength and a second light wave having a second, different wavelength. The first light wave may change the optical parameters of the vascular tissue or a component of blood within the vascular tissue to increase the absorption of the second light wave by the vascular tissue or the component of blood within the vascular tissue.

In some embodiments, the method further includes forming the light into at least one light beam. In other embodiments, the method further includes forming the light into at least two light beams that propagate at different angles with respect to the deformed vascular tissue.

In some embodiments, the light may be configured to penetrate the vascular tissue through a surface of the vascular tissue while maintaining the original integrity of the surface of the vascular tissue. In other embodiments, the light may be configured to penetrate the vascular tissue through a cut in the vascular tissue formed prior to or during sealing of the vascular tissue.

In some embodiments, illuminating the at least one portion of the vascular tissue with light includes illuminating the at least one portion of the vascular tissue with light all at one time. In other embodiments, illuminating the at least one portion of the vascular tissue with light includes forming the light into at least one light spot and scanning the at least one light spot over the at least one portion of the vascular tissue.

The method may further include monitoring at least one parameter of the vascular tissue and controlling at least one parameter of the light based on the at least one parameter of the vascular tissue. The at least one parameter of the light may include one or more of intensity, frequency, polarization, phase, pulse width, pulse frequency, duty cycle, repetition rate, wave shape, duration of illumination, total exposure of tissue to the light, or the spectra of the light. Also, the at least one parameter of the vascular tissue may include one or more of the electrical impedance of a volume of the vascular tissue, the optical transparency of the vascular tissue, the degree of optical anisotropy of the vascular tissue, or the polarization-dependent optical loss in the vascular tissue. In some embodiments, the method may further include sensing the temperature of the vascular tissue and controlling at least one parameter of the light based on the temperature of the vascular tissue.

In some embodiments, deforming the vascular tissue includes stretching the vascular tissue along a longitudinal axis of a vessel within the vascular tissue. In other embodiments, deforming the vascular tissue includes compressing the vascular tissue.

In another aspect, the present disclosure features an energy-based instrument for sealing vascular tissue. The energy-based instrument includes a deforming member for deforming vascular tissue and an optical system for illuminating a portion of the vascular tissue with light to seal the vascular tissue. The optical system includes a light source for generating light, a light distribution element for distributing the light over the portion of the vascular tissue, and a light guide for guiding the light from the light source to the light distribution element.

The deforming member of the energy-based instrument may include at least a first deforming member and a second deforming member for moving in opposite directions and for deforming vascular tissue placed between the first deforming member and the second deforming member. At least one of the first deforming member and the second deforming member may include optical reflective material for reflecting the light and for causing the light to pass through the vascular tissue at least twice. Also, at least one portion of at least one of the first deforming member and the second deforming member may be transparent to the light.

In some embodiments, a portion of at least one of the first deforming member and the second deforming member does not contact the portion of the deformed vascular tissue that is illuminated with the light. The light distribution element may be optically coupled to at least one of the first deforming member and the second deforming member.

The energy-based instrument may further include a sensor for sensing at least one parameter of the vascular tissue and a controller for controlling at least one parameter of the light generated by the light source based on the at least one parameter of the vascular tissue sensed by the sensor. The at least one parameter of the light may include one or more of intensity, frequency, polarization, phase, pulse width, pulse frequency, duty cycle, repetition rate, wave shape, duration of illumination, total exposure of tissue to the light, or the spectra of the light.

The light source of the energy-based instrument may include at least one light emitting diode or at least one laser. The at least one laser may generate light having different wavelengths. Also, the at least one laser may be a tunable laser that is tuned to generate light of a desired wavelength.

The light distribution element of the energy-based instrument may be configured to create conditions of frustrated total internal reflection. The light distribution element may include at least one lens, at least one prism, at least one waveguide structure, or at least one periodic optical structure. The at least one periodic optical structure may be a diffraction grating, such as a Bragg diffraction grating. In some embodiments, the light guide includes at least one waveguide structure, such as an optical fiber.

In yet another aspect, the present disclosure features an energy-based instrument for cutting and sealing vascular tissue. The energy-based instrument includes a deforming member for deforming vascular tissue to cause different layers of the vascular tissue to contact each other and a cutting member for cutting the vascular tissue and illuminating at least one portion of the vascular tissue with light to seal at least one cut surface of the vascular tissue.

The deforming member may include a first deforming member and a second deforming member configured to move in opposite directions and to deform vascular tissue placed between the first deforming member and the second deforming member. The cutting member may be a movable cutting member and at least one of the first deforming member and the second deforming member may include a recess to guide the moveable cutting member to cut the vascular tissue.

The energy-based instrument may further include a light source for generating light. The cutting member may include an optical beam former coupled to the light source. The optical beam former may form the light into a light beam to cut the vascular tissue. In other embodiments, the cutting member includes a cutting edge that mechanically cuts the vascular tissue.

The cutting member may include an optical waveguide for guiding light through at least one side of the cutting member and illuminating the vascular tissue with the light to seal the at least one cut surface of the vascular tissue. The optical waveguide may be configured to create conditions of frustrated total internal reflection on at least one side of the optical waveguide.

The optical waveguide may include a light distribution element for distributing light on at least one cut surface of the vascular tissue through at least one side of the optical waveguide. The light distribution element may include at least one periodic optical structure.

In yet another aspect, the present disclosure features a method of cutting vascular tissue. The method includes deforming vascular tissue to cause different layers of the vascular tissue to contact each other, cutting the deformed vascular tissue, and illuminating the deformed vascular tissue with light to seal at least one cut surface of the vascular tissue.

The method may further include generating light sufficient to cut the deformed vascular tissue, forming the light into a light beam, and applying the light beam to the vascular tissue to cut the deformed vascular tissue.

In some embodiments, cutting the deformed vascular tissue includes applying mechanical force to a cutting member to cut the deformed vascular tissue. In other embodiments, cutting the deformed vascular tissue includes cutting the deformed vascular tissue with a cutting member and illuminating the deformed vascular tissue with light includes forming a light beam within a cutting member and illuminating the deformed vascular tissue with the light beam through at least one side of the cutting member. The step of illuminating the deformed vascular tissue with light may include creating conditions of frustrated total internal reflection on at least one side of an optical waveguide within the cutting member.

In some embodiments, deforming the vascular tissue includes stretching the vascular tissue along a longitudinal axis of a vessel within the vascular tissue. In other embodiments, deforming the vascular tissue includes compressing the vascular tissue.

BRIEF DESCRIPTION OF THE DRAWINGS

Various embodiments will be described herein below with reference to the drawings wherein.

DETAILED DESCRIPTION

As described above, existing methods of heating and sealing vascular tissue (e.g., vessels) using electromagnetic radiation in the radio frequency (RF) range may have some drawbacks. These drawbacks may include stray currents, flashover, short circuits, the need for electrical insulation, and interference with other tissues, organs, and medical devices. Using light to heat and seal vascular tissue avoids these drawbacks while also maintaining the integrity of the tissue. The term "light" as used in the present disclosure refers to electromagnetic radiation in the infrared, visible, and ultraviolet regions of the electromagnetic spectrum.

According to embodiments of the present disclosure, tissue sealing is accomplished by deforming the vascular tissue to provide direct contact between different layers of the vascular tissue and illuminating the vascular tissue with light. Absorption of the light by the tissue causes the heating of the vascular tissue followed by the melting or denaturizing of the collagen and elastin in the vascular tissue. Deforming the vascular tissue through mechanical impact facilitates the release and mixture of collagen and elastin from the vascular tissue. When the light is removed from the vascular tissue, the melted collagen and elastin reform to create a permanent vascular tissue seal.

Figure 1:
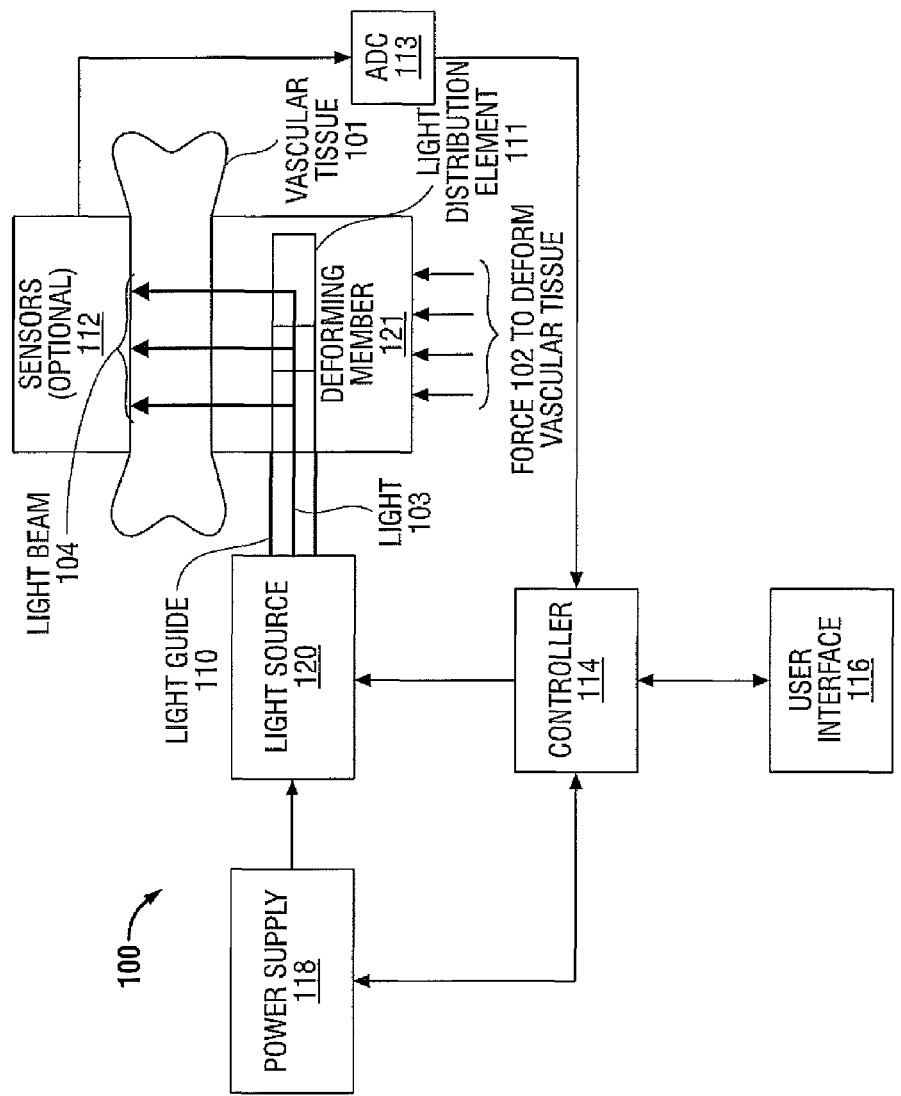
FIG. 1 is a block diagram of an optical sealing system according to embodiments of the present disclosure.

FIG. 1 is a block diagram of a vascular tissue sealing system 100 according to embodiments of the present disclosure. The system 100 includes a light source 120, a light guide 110, a light distribution element 111, and a deforming member 121, which operate together to form a high-quality tissue seal. The deforming member 121 applies a force 102 to deform the vascular tissue 101 and bring different layers of the vascular tissue 101 into direct physical contact with each other. Then, the light source 120 generates light 103 and provides it to the light distribution element 111 via the light guide 110. The light distribution element 111, which may be incorporated into the deforming member 121, forms the light 103 into a light beam 104 and illuminates the vascular tissue 101 with the light beam 104. The light beam 104 heats the deformed vascular tissue 101 to create a tissue seal.

The vascular tissue sealing system 100 also includes a control system that incorporates feedback to control the tissue sealing process. The control system may use the feedback to optimize the tissue sealing process, e.g., to determine optimal exposure, to minimize thermal damage, and to reduce energy consumption. For example, the control system may use the feedback to adjust amplitude-time characteristics of the light 103 (e.g., amplitude, number of pulses, pulse duration, and pulse repetition rate) to obtain a desired tissue seal quality and to avoid tissue charring or destruction.

Figure 3:
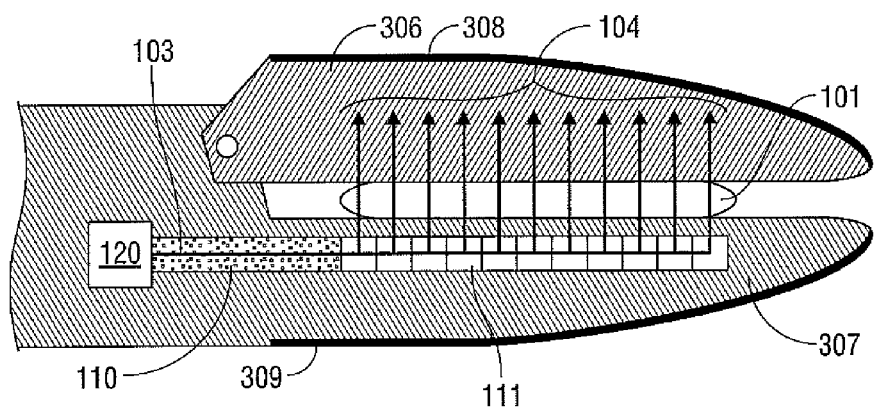
FIG. 3 is a cross-sectional side view of a portion of an instruments used to seal vascular tissue according to some embodiments of the present disclosure.
Figure 4:
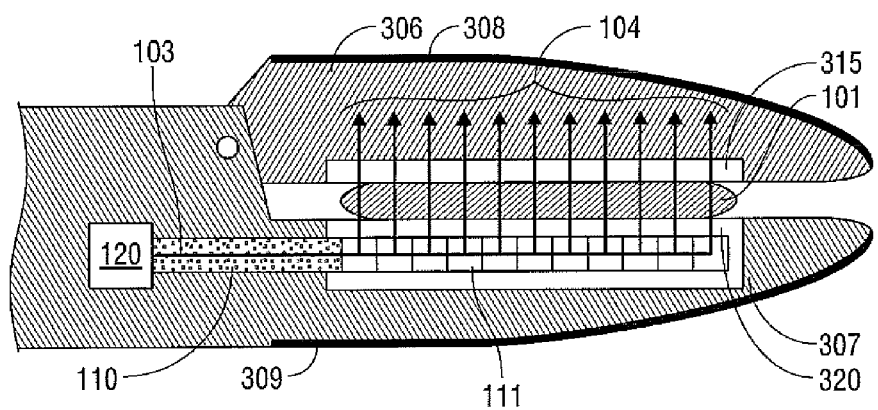
FIG. 4 is a cross-sectional side view of a portion of an instrument used to seal vascular tissue according to other embodiments of the present disclosure.

The feedback may include on one or more optical, electrical, or other parameter of the vascular tissue. For example, the feedback may include electrical impedance, optical transparency, optical polarization-dependent loss, or temperature of the vascular tissue. The feedback may also include one or more parameters of the electrical, optical, and mechanical subsystems of the vascular tissue sealing system 100. For example, the feedback may include the gap distance between opposing sealing surfaces of the jaw members 306, 307 (as shown in FIGS. 3 and 4) and the pressure applied to the vascular tissue 101. These parameters should be accurately controlled to assure a consistent and reliable seal.

The control system of the vascular tissue sealing system 100 may include sensors 112, an analog-to-digital converter (ADC) 113, a controller 114, a user interface 116, and a power supply 118. The sensors 112 sense one or more optical, electrical, or other parameters of the vascular tissue 101 and transmit sensor information in the form of analog sensor signals to the ADC 113. For example, the sensors 112 may sense optical parameters of the tissue 101 including the optical transparency of the tissue 101, the degree of reflection from the tissue 101, the optical loss resulting from absorption and/or scattering by the tissue 101 (e.g., the optical polarization dependent losses in the tissue 101), the degree of anisotropy of the optical parameters, or any combination of these optical parameters as disclosed in commonly-owned U.S. patent application Ser. No. 13/108,129, entitled "System and Method for Energy-Based Sealing of Tissue with Optical Feedback," the entire contents of which are incorporated by reference herein. In some embodiments, the sensors 112 may include an optical sensor system as disclosed in commonly-owned U.S. patent application Ser. No. 12/757,340, entitled "Optical Hydrology Arrays and System and Method for Monitoring Water Displacement During Treatment of Patient Tissue," the entire contents of which are incorporated by reference herein. The sensors 112 may also sense one or more parameters of the light beam 104.

The ADC 113 converts the analog sensor signals to digital sensor data and transmits the digital sensor data to the controller 114. The controller 114 processes the digital sensor data and regulates one or more parameters of the light 103 by transmitting appropriate control signals to the light source 120. In some embodiments, the ADC 113 is incorporated into the controller 114 and the sensors 112 transmit the analog sensor signals to the controller 114 via a wireless communications link.

The user interface 116, which may be local to or remote from the controller 114, is coupled to the controller 114 via a communications link to allow the user to control various parameters of the light beam 104 applied to the vascular tissue 101 during a sealing procedure. The user may manually set one or more parameters of the light 103 and/or the light beam 104 and the controller 114 may regulate and/or control these parameters. The one or more parameters of the light 103 and/or the light beam 104 may include intensity, frequency, polarization, phase, pulse width, pulse frequency, duty cycle, repetition rate, wave shape, duration of illumination, total exposure of tissue to the light beam 104, or the spectra of the light 103 and/or the light beam 104. The intensity of the light 103 and/or the light beam 104 may include total intensity and/or spatial distribution of intensity over the illuminated tissue. A user may enter data into the user interface 116 such as the type of instrument, the type of surgical procedure, and/or the tissue type.

The controller 114 is also coupled to the power supply 118 (e.g., a DC power supply) via a communications link to enable the controller 114 to control and monitor the power supplied by the power supply 118 to the light source 120. The controller 114 may receive feedback signals from the power supply 118, may generate control signals based on the feedback signals, and may transmit these control signals to the power supply 118. The control signals may control the magnitude of the voltage and current output from the power supply 118. The control signals may also be converted to analog signals by a digital-to-analog converter (DAC) (not shown) before they are applied to the power supply 118.

The controller 114 may include at least one microprocessor capable of executing software instructions for processing data received from the user interface 116 and the sensors 112 and for outputting appropriate control signals to the light source 120 and/or the power supply 118. The software instructions executed by the at least one microprocessor may be stored in an internal memory of the controller 114, an internal or external memory bank accessible by the controller 114, and/or an external memory, e.g., an external hard drive, floppy diskette, or CD-ROM.

The system 100 may be implemented as a single surgical device, such as a portable surgical device, or a surgical device broken up into separate components. For example, the system 100 may include two components: (1) a controller console, which may include the ADC 113, controller 114, user interface 116, and power supply 118, and (2) an instrument, which may include the light source 120, light guide 110, deforming member 121, and sensors 112.

Figure 2:
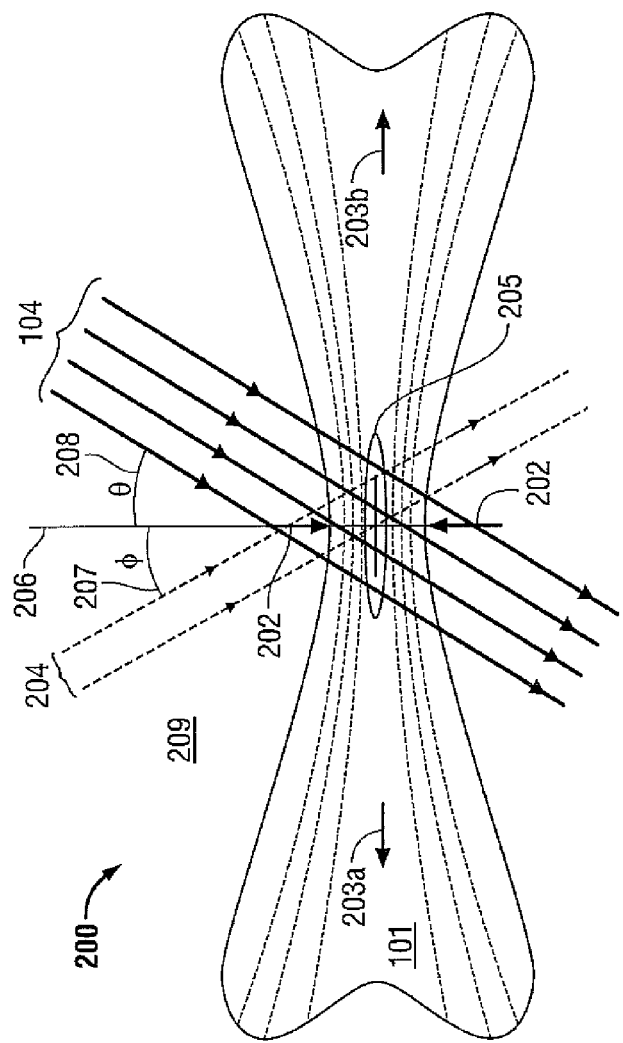
FIG. 2 is an illustration of a method of sealing vascular tissue according to embodiments of the present disclosure.

FIG. 2 is an illustration 200 showing a method of sealing vascular tissue 101 in accordance with embodiments of the present disclosure. The method involves deforming the vascular tissue 101 and exposing at least a portion of the deformed tissue to a light beam 104. Deforming the vascular tissue 101 brings different layers of the vascular tissue 101, including opposite walls of a vessel 205, into direct contact with each other. Also, deforming the vascular tissue 101 partially destroys layers of the vascular tissue 101 to facilitate extraction of collagen and elastin from the interlayer space. Finally, deforming the vascular tissue 101 displaces blood or other biological fluids and reduces the volume of vascular tissue to be sealed.

The vascular tissue 101 may be deformed by compressing the vascular tissue 101, e.g., by applying mechanical force to opposite sides of the vascular tissue 101 as indicated by the arrows 202. Alternatively or in addition to compressing the vascular tissue 101, the vascular tissue 101 may be deformed by extending or stretching the vascular tissue 101 in a direction perpendicular to an axis 206, which is perpendicular to the surface of the vascular tissue 101. For example, the vascular tissue 101 may be deformed by pulling a first portion of the vascular tissue 101 in a first direction 203a while pulling a second portion of the vascular tissue 101 in a second direction 203b (i.e., in the opposite direction). The vascular tissue 101 may also be deformed by twisting the vascular tissue 101 or by applying pressure at different locations on the vascular tissue 101.

As illustrated in FIG. 2, the light beam 104 illuminates the vascular tissue 101 at an incidence angle θ208 with respect to the axis 206. The light beam 104 includes at least one spectral component that is within the range of the absorption spectra of the tissue so that the light beam 104 can heat and seal the vascular tissue 101. The incidence angle θ208 of the light beam 104 may be variable to allow for adjustment of the light penetration depth and other optical parameters. For example, increasing the angle θ208 of the light beam 104 decreases the amount of light energy absorbed by the vascular tissue 101. To vary the angle θ208 of the light beam 104, the system 100 of FIG. 1 may include a light distribution element 111 configured to adjust the angle θ208 of the light beam 104 in response to appropriate control signals from the controller 114.

In some embodiments, the light distribution element 111 and the deforming member 121 of FIG. 1 are configured to create conditions of frustrated total internal reflection. To create these conditions, the refractive index of the ambient medium 209 (e.g., air) is selected to be less than the refractive index of the vascular tissue 101. Also, the light distribution element 111 directs the light beam 104 at an angle with respect to an axis normal to the surface of the deforming member 121. The angle may be selected to create total internal reflection within the deforming member 121. In other words, the angle is selected to cause the entire light beam 104 to reflect off of the boundary between the deforming member 121 and the ambient medium 209. When the deforming member 121 gets close enough to the vascular tissue 101, there is a transition to frustrated total internal reflection in which the light beam 104 passes energy from the deforming member 121 across the ambient medium 209 to the vascular tissue 101. This configuration may reduce the light penetration depth and thus increase the localization of induced heating of the vascular tissue 101.

The light beam 104 may be spatially distributed in a manner that provides an appropriate distribution of absorbed light energy in the tissue to be sealed. The entire target tissue volume may be exposed to light all at once or it may be scanned with a light spot or multiple light spots. In the case of scanning, less light power may be needed and the parameters of the light may be adjusted to the local parameters of the vascular tissue 101, thus reducing thermal damage. Spatially localized exposure may also be used to provide a sealing mode similar to spot welding. In this case, the tissue is sealed locally in a number of discrete spots.

To more efficiently heat the vascular tissue 191, the light beam 104 may have several different wavelengths. The wavelengths can be selected so that light at one of the wavelengths is absorbed by hemoglobin or other blood components, which causes the hemoglobin or other blood components to absorb light at other wavelengths, which have low absorption by tissue in its initial state prior to illumination.

The use of different wavelengths of light also enables selective heating of different tissues. For example, tissue containing fat and blood vessels may be exposed to green light and near-infrared (IR) light. Fat has a low absorption of green light, whereas blood vessels have a high absorption of green light and thus heat up when illuminated by green light. The heating of the blood vessels by the green light causes the coagulation of hemoglobin and creates an absorption center for near IR radiation. As the coagulated hemoglobin absorbs the near IR radiation, it increases in temperature and heats the blood vessels.

The light may also include at least two light beams that illuminate the vascular tissue at different angles. For example, as shown in FIG. 2, a second light beam 204 may illuminate the vascular tissue 101 at an angle ϕ207 with respect to the axis 206.

As described above, an apparatus or instrument for vascular tissue sealing according to embodiments of the present disclosure includes both components that deform vascular tissue and components that expose the vascular tissue to light. In some embodiments, the instrument includes at least two members by which force is applied to the vascular tissue to grip, hold, and deform the vascular tissue (e.g., blood vessels or bile ducts) to bring different layers of the vascular tissue into contact with each other.

FIG. 3 shows an embodiment of an instrument having two jaw members 306, 307 (i.e., two deforming members). The jaw members 306, 307 are configured to move with respect to each other (e.g., the upper jaw member 306 may move while the lower jaw member 207 remains stationary) and to directly contact the vascular tissue 101. The jaw members 306, 307 can grasp, hold, and compress the vascular tissue 101 to bring different layers of the vascular tissue 101 into direct contact with each other, to partially destroy layers of the vascular tissue 101, and to stop the flow of fluid in a vessel (e.g., the vessel 205 of FIG. 2).

The bottom jaw member 307 is made of a material that is at least partly transparent to the light beam 104 to allow the light beam 104 to pass through a portion of the jaw member 307 to the vascular tissue 101. The top jaw member 306 may also be made of a transparent material that is at least partly transparent to the light beam 104 to allow the light beam 104 to pass through the top jaw member 306 to the eyes of a surgeon. As a result, the surgeon can view the vascular tissue 101 and the vessels 205 grasped between jaw members 306, 307. This enables the surgeon to more accurately and easily position the jaw members 306, 307 and to control the sealing process and ultimately the quality of the tissue seal.

As shown in FIG. 3, the jaw members 306, 307 make direct contact with the vascular tissue 101. In some instances, the tissue may adhere to the inside surface of the jaw members 306, 307. To prevent this, the jaw members 306, 307 may include an optically-transparent coating with low adhesion to tissue, such as optically-transparent collagen.

The light source 120 may include one or more lasers, e.g., a semiconductor laser or a fiber laser. The spectrum of the laser radiation may contain one or more spectral components that lie within the absorption range of the vascular tissue 101. The light guide 110 delivers the light 103 generated by the light source 120 to a light distribution element 111. The light guide 110 may include an optical waveguide such as an optical fiber or a bundle of optical fibers.

The light distribution element 111 receives the light 103 from the light guide 110 and forms the light 103 into a light beam 104. To form the light beam 104, the light distribution element 111 may include a prism or an appropriate waveguide structure. The light distribution element 111 may also include a spatially periodic optical structure such as an amplitude-phase grating or a long-period fiber Bragg grating.

The wavelength of the light 103 emitted from the light source 120 may be tuned to vary the diffraction pattern created by the spatially-periodic optical structure of the light distribution system 111. For example, the wavelength of the light 103 may be tuned to vary the direction of propagation of the diffracted light (i.e., the light beam 104) to adjust the light penetration depth and the amount of light energy transmitted to the vascular tissue 101. In this way, the heating of the vascular tissue 101 may be controlled.

To increase the efficient use of light energy, reflective components may be used to cause the light beam 104 to pass through the tissue being sealed multiple times. For example, as shown in FIG. 3, the outer surface of the upper jaw member 306 may include a reflective coating 308 and the outer surface of the lower jaw member 307 may include a reflective coating 309. In this embodiment, the light beam 104 emitted from the spatially periodic optical structure of the light distribution system 111 may pass through the vascular tissue 101, reflect off of the reflective coating 308, pass again through the vascular tissue 101, reflect off of the reflective coating 309, pass again through the vascular tissue 101, and so forth. To allow a surgeon to see the vascular tissue 101 through the transparent jaw members 306, 307, the reflective coatings 308, 309 may be made of a spectrally selective material that reflects the light used to seal the vessel (e.g., near IR light), but transmits visible light.

The jaw members 306, 307 may be made of material with low thermal conductivity because, unlike RF-based sealing methods and instruments, the systems, instruments, and methods according to embodiments of the present disclosure do not require electrically conductive electrodes, which typically have high thermal conductivity. When metal electrodes with high thermal conductivity come into physical contact with vascular tissue, a significant amount of heat is lost through the body of the instrument. Because the jaw members 306, 307 are not heated by the light, the jaw member material can be selected to have low adhesion to the vascular tissue or a transparent lubricant may be applied to the inner surfaces of the jaw members 306, 307 to prevent the vascular tissue 101 from adhering to the jaw members 306, 307.

Figure 5:
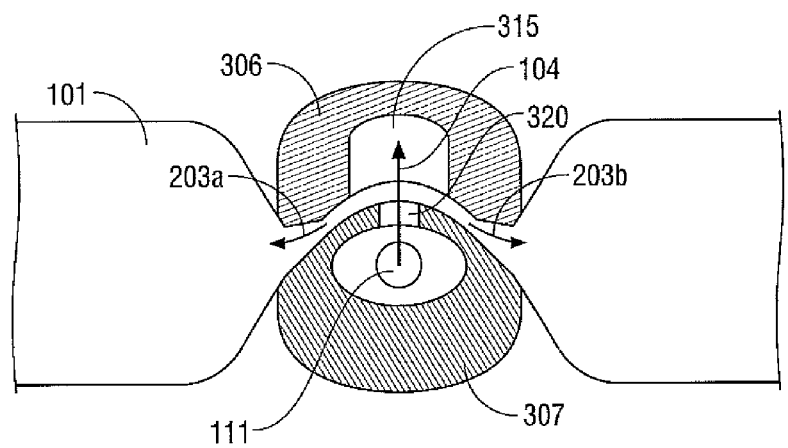
FIG. 5 is a cross-sectional front view of the instrument of FIG. 4.

FIGS. 4 and 5 show cross-sectional side and front views of an instrument for sealing vascular tissue. In this embodiment, the jaw members 306, 307 deform the vascular tissue 101 by extending or stretching the vascular tissue 101 along the length-wise axis of the vascular tissue 101 rather than compressing the vascular tissue 101, to intensify the release of elastin and collagen. The upper jaw member 306 includes two sides that define a cavity 315 and are shaped to mate with the rounded upper portion of the lower jaw member 307. The lower jaw member 307 includes an aperture 320 through which a light beam 104 passes from the light distribution element 311 to the cavity 315.

As the jaw members 306, 307 are brought together to deform the vascular tissue 101, the two sides of the upper jaw member 306 stretch or extend the vascular tissue 101 that is to be illuminated by the light beam 104 across the upper portion of the lower jaw member 307 by pulling the surrounding tissue in opposite directions 203a, 203b. Consequently, the different layers of vascular tissue 101 (e.g., the opposite walls of the vessel 205 of FIG. 2) are made thinner and are brought into contact with each other.

The advantage of this embodiment is that there is no direct physical contact between the jaw members 306, 307 and that portion of the vascular tissue 101 that is illuminated by the light beam 104. Similar to FIG. 3, the instrument includes a light distribution element 111 disposed in the lower jaw member 307 a predetermined distance from the vascular tissue 101. The light distribution element 111 forms a light beam 104 and illuminates the vascular tissue 101 through the aperture 320. The light distribution element 111 may include optical fibers, lenses, and/or prisms optically coupled to a light source (e.g., the light source 120 of FIG. 3) via a light guide (e.g., the light guide 110 of FIG. 3). The optical fibers may contain a grating structure to distribute the light beam 104 out of the side of the optical fibers along a predetermined length of the optical fibers.

The propagation direction and the wavelength of the light 104 are selected to provide the desired tissue penetration depth by the light beam 104. Since neither the light distribution element 111 nor the jaw members 306, 307 have direct physical contact with that portion of the tissue that is illuminated by the light beam 104, the sealed vascular tissue never adheres to any portion of the instrument. In this manner, the jaw members 306, 307 and the light distribution element 111 avoid contamination by the sealed vascular tissue 101.

Figure 6:
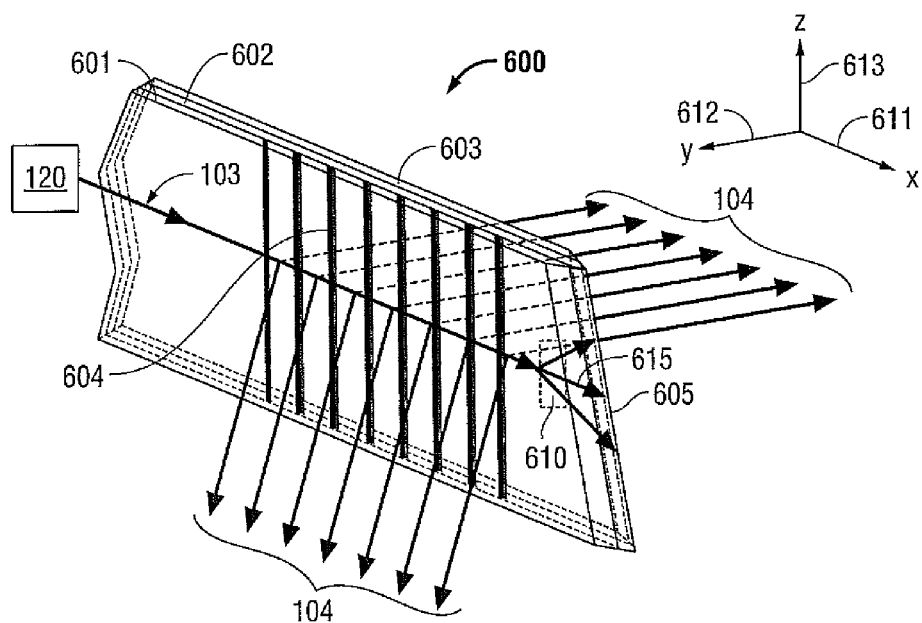
FIG. 6 is a perspective view of a cutting member according to yet other embodiments of the present disclosure.

FIG. 6 shows a cutting member 600 of an instrument for vascular tissue sealing that includes a waveguide having three layers 601-603, a light distribution element 604, and a cutting edge 605. As the cutting edge 605 cuts through vascular tissue 101, the light distribution element 604 receives light 103, forms a light beam 104, and illuminates the cut surfaces of the layers of vascular tissue 101 with the light beam 104 through the sides of the cutting member 600. Accordingly, the cutting member 600 allows a user to simultaneously cut vascular tissue 101 using the cutting edge 605 and seal vascular tissue 101 using the light beam 104.

As shown in FIG. 6, layers 601, 603 form the walls of the waveguide and layer 602 is the medium through which the light 103 propagates. The cutting member's waveguide is optically coupled to the light source 120, which generates the light 103. In some embodiments, the cutting member 600 may itself include a light source (e.g., semiconductor lasers) that generates the light 103. The waveguide 601-603 directs the light 103 generated by the light source to the light distribution element 604 in a direction 611 parallel to the x-axis 611. The light distribution element 604, in turn, directs and distributes the light beam 104 through the side of the cutting edge 605 across the layers of vascular tissue 101 that are cut by the cutting edge 605. In this manner, the cutting member 600 can more completely and uniformly illuminate the layers of the vascular tissue 101 with the light beam 104.

The light source 120 may generate light 103 having multiple light rays that impinge on all or a portion of the light distribution element 604. The light distribution element 604, in turn, would form the light 103 into a light beam that spans not only the length of the light distribution element 604 (i.e., the dimension of the light distribution element 604 along the x-axis 611), but also at least a portion of the height of the light distribution element 604 (i.e., the dimension of the light distribution element 604 along the z-axis 613). For example, the light source 120 may generate light 103 having multiple light rays that impinge on the entire area (i.e., length times width) of the light distribution element 604, in which case the light distribution element 604 would form a light beam having a cross section defined by the area of the light distribution element 604.

Alternatively, or in combination with the cutting edge 605, the cutting member 600 may use optical energy to cut the tissue 101. For example, the cutting member 600 includes an optical cutting element 610 that forms the light 103 or light from a separate light source into a light beam 615 that can cut the tissue 101.

As also shown in FIG. 6, the light distribution element 604 is a spatial periodic optical structure such as a grating structure. The spatial periodic optical structure diffracts the light so that it penetrates the layers of cut vascular tissue 101 at a predetermined angle. In other embodiments, instead of a spatial periodic optical structure, the light distribution element 604 includes other reflective or refractive materials configured to redirect and distribute the light 104 across the cut layers of the vascular tissue 101. For example, the reflective or refractive materials may be configured to create conditions of frustrated total internal reflection at the outer surfaces of the waveguide's outer layers 601, 603. In this configuration, the light beam 104 passes energy from the cutting member 600 across the ambient medium (i.e., air) to the vascular tissue 101 when the outer surfaces of the cutting member 600 are near enough to the vascular tissue 101.

Figure 7:
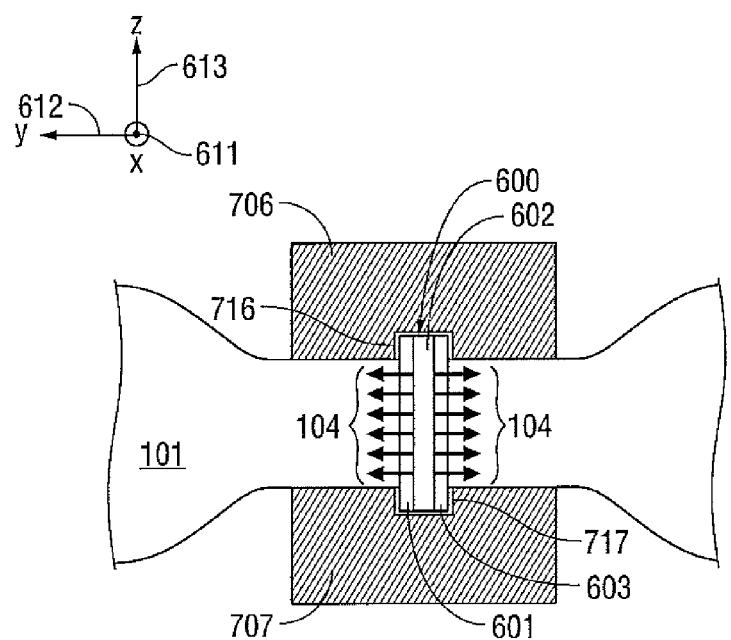
FIG. 7 is a cross-sectional front view of the cutting member of FIG. 6 in an instrument used to seal and cut vascular tissue according to certain embodiments of the present disclosure.

FIG. 7 shows a front cross-sectional view of the cutting member 600 of FIG. 6 that is incorporated into a surgical instrument having jaw members 706, 707 for grasping, compressing, and holding the vascular tissue 101. The jaw members 706, 707 include recesses 716, 717 extending along the length (i.e., along the x-axis 611) of the jaw members 706, 707 to guide the movement of the cutting member 600 along the x-axis 611.

At the start of a tissue sealing procedure, the jaw members 706, 707 grasp, compress, and hold the vascular tissue 101. While the jaw members 706, 707 hold the vascular tissue 101, the cutting member 600 is moved along the x-axis 611 to cut the vascular tissue 101. At the same time, the light distribution element 604 directs and distributes a light beam 104 across the surfaces of the cut vascular tissue 101. As described above, the light distribution element 604 may distribute light 103 along both a portion of the length of the cutting member 600 as shown in FIG. 6 (i.e., along the length of the light distribution element 604) and a portion of the height of the cutting member 600 as shown in FIGS. 6 and 7 (i.e., along the height of the light distribution element 604 as shown in FIG. 6). In other words, the light distribution element 604 may distribute the light 104 so that it illuminates a cross-sectional area of cut tissue.

Figure 8:
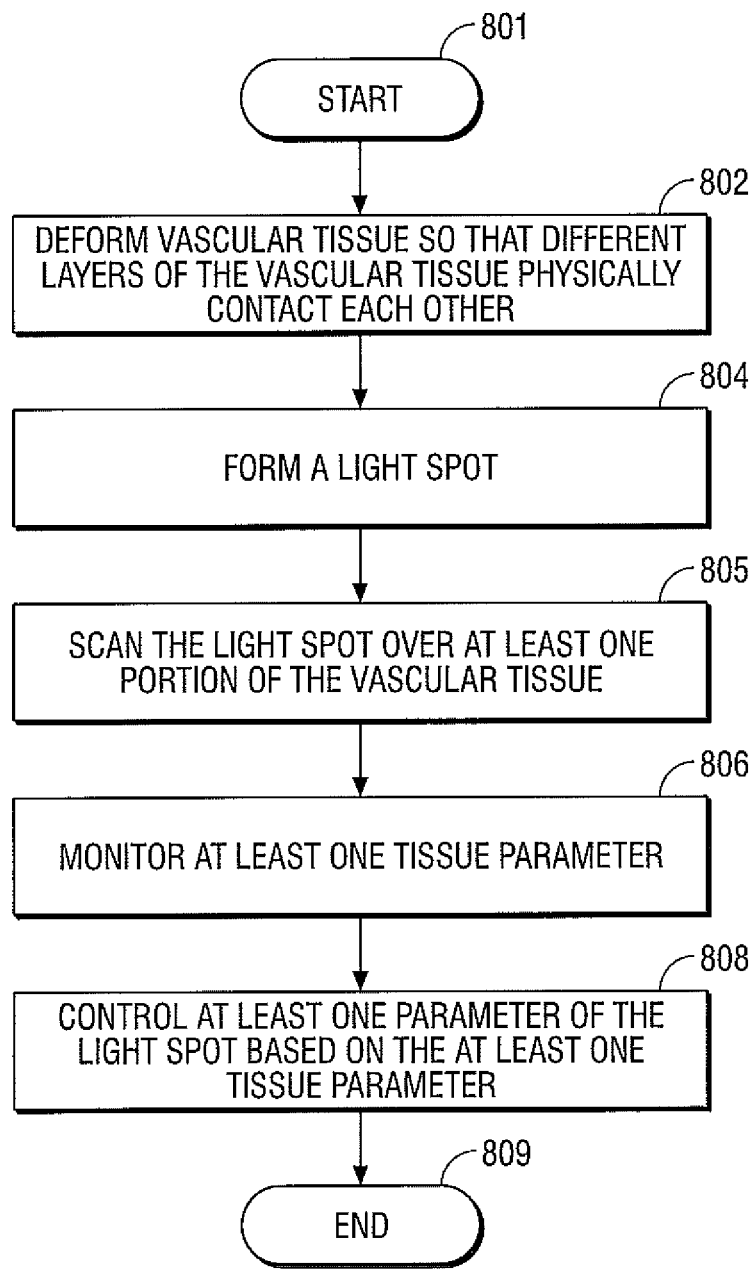
FIG. 8 is a flow diagram of a method of sealing vascular tissue according to some embodiments of the present disclosure.

FIG. 8 is a flow diagram of a method or process of sealing vascular tissue by scanning the vascular tissue with a light spot according to some embodiments of the present disclosure. After starting in 801, vascular tissue is deformed in step 802 so that different layers of the vascular tissue physically contact each other. In step 804, a light spot is formed, and, in step 805, the light spot is scanned over at least one portion of the vascular tissue. While the light spot is scanned over the vascular tissue, at least one tissue parameter is monitored in step 806. For example, the tissue temperature may be monitored. Then, at least one parameter of the light spot is controlled 808 based on the at least one tissue parameter monitored in step 806. For example, the intensity of the light spot may be varied based on the monitored tissue temperature. Finally, the process ends in step 809.

Although this disclosure has been described with respect to particular embodiments, it will be readily apparent to those having ordinary skill in the art to which it appertains that changes and modifications may be made thereto without departing from the spirit or scope of the disclosure. For example, the controller 114 of FIG. 1 may include circuitry and other hardware, rather than, or in combination with, programmable instructions executed by a microprocessor for processing the sensed information and determining the control signals to transmit to the power supply 118 and/or the light source 120.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of particular embodiments.

What is claimed is:

1. An energy-based instrument for cutting and sealing vascular tissue, comprising:
    first and second deforming members configured to move in opposite directions and configured to deform vascular tissue placed between the first and second deforming members to cause different layers of the vascular tissue to contact each other; and a cutting blade moveable with respect to the first and second deforming members in a direction different from directions of movement of the first and second deforming members, and configured to cut the vascular tissue, the cutting blade including a first layer, a second layer, a third layer disposed between the first layer and the second layer, and a light distribution element disposed between the first layer and the second layer, the third layer defining a cutting edge at a distal end of the cutting blade, the light distribution element being configured to receive light propagating through the third layer and to distribute light through at least one of the first and second layers of the cutting blade to illuminate at least one cut surface of the vascular tissue with light to seal the at least one cut surface of the vascular tissue.

2. The energy-based instrument of claim 1, wherein at least one of the first deforming member or the second deforming member includes a recess to guide the cutting blade to cut the vascular tissue.

3. The energy-based instrument of claim 1, further comprising a light source configured to generate light, wherein the cutting edge of the cutting blade includes an optical beam former coupled to the light source, the optical beam former configured to form light into a light beam to cut the vascular tissue.

4. The energy-based instrument of claim 1, wherein the cutting blade includes a cutting edge that mechanically cuts the vascular tissue.

5. The energy-based instrument of claim 1, wherein the cutting blade includes an optical waveguide configured to guide light to the cutting edge.

6. The energy-based instrument of claim 5, wherein the optical waveguide is configured to create conditions of frustrated total internal reflection on at least one side of the optical waveguide.

7. The energy-based instrument of claim 5, wherein the light distribution element distributes the light on the at least one cut surface of the vascular tissue though at least one side of the optical waveguide.

8. The energy-based instrument of claim 7, wherein the light distribution element includes at least one periodic optical structure.

9. The energy based instrument of claim 1, wherein the at least one cut surface of the vascular tissue is illuminated with light in a direction different from the directions of movement of the first and second deforming members and from the direction of movement of the cutting blade.

10. A method of cutting vascular tissue, comprising:
moving first and second deforming members in opposite directions to deform vascular tissue placed between the first and second deforming members to cause different layers of the vascular tissue to contact each other;
moving a cutting blade with respect to the first and second deforming members in a direction different from directions of movement of the first and second deforming members to cut the deformed vascular tissue, wherein the cutting blade includes a first layer, a second layer, a third layer disposed between the first layer and the second layer, and a light distribution element disposed between the first layer and the second layer, the third layer defining a cutting edge at a distal end of the cutting blade;
receiving, by the light distribution element, light propagating through the third layer; and
distributing, by the light distribution element, light through at least one of the first and second layers of the cutting blade to illuminate at least one cut surface of the vascular tissue with light to seal the at least one cut surface of the vascular tissue.

11. The method of claim 10, further comprising:
generating light sufficient to cut the deformed vascular tissue;
forming the light into a light beam; and
applying the light beam to the vascular tissue to cut the deformed vascular tissue.

12. The method of claim 10, wherein cutting the deformed vascular tissue includes applying mechanical force to the cutting blade to cut the deformed vascular tissue.

13. The method of claim 10, wherein distributing the light includes forming a light beam within the cutting blade and illuminating the deformed vascular tissue with the light beam through the at least one of the first and second layers of the cutting blade.

14. The method of claim 13, wherein illuminating the deformed vascular tissue with light includes creating conditions of frustrated total internal reflection on at least one side of an optical waveguide within the cutting blade.

15. The method of claim 10, wherein deforming the vascular tissue includes stretching the vascular tissue along a longitudinal axis of a vessel within the vascular tissue.

16. The method of claim 10, wherein deforming the vascular tissue includes compressing the vascular tissue.

17. The method of claim 10, wherein the at least one cut surface of the vascular tissue is illuminated with light in a direction different from the directions of movement of the first and second deforming members and from the direction of movement of the cutting blade.

* * * * *